United States Patent [19]

Bany et al.

[11] Patent Number: 5,019,071
[45] Date of Patent: May 28, 1991

[54] ADHESIVE FASTENING TAB

[75] Inventors: Stephen W. Bany, St. Paul; John A. Miller, Woodbury; Brad W. Eaton, St. Paul, all of Minn.

[73] Assignee: Minnesota Mining and Manufacturing Company, St. Paul, Minn.

[21] Appl. No.: 449,592

[22] Filed: Dec. 12, 1989

[51] Int. Cl.$^5$ .................. A61F 13/15; C08J 53/00; C08K 53/00; C08L 53/00
[52] U.S. Cl. .................................. 604/389; 524/505
[58] Field of Search ........................ 604/390; 524/505

[56] References Cited

U.S. PATENT DOCUMENTS

| | | | |
|---|---|---|---|
| T100,203 | 1/1981 | Lauck | 428/40 |
| 3,239,478 | 3/1966 | Harlan | 524/505 |
| 3,635,861 | 1/1972 | Russel | 260/27 |
| 3,676,202 | 7/1972 | Korpman | 117/122 P |
| 3,787,531 | 1/1974 | Dahlquist et al. | 260/876 B |
| 3,797,495 | 3/1974 | Schmidt | 128/287 |
| 3,862,068 | 1/1975 | Russell | 260/27 |
| 3,932,328 | 1/1976 | Korpman | 260/27 BB |
| 3,935,338 | 1/1976 | Robertson | 427/207 |
| 3,954,692 | 5/1976 | Downey | 260/33.6 AQ |
| 3,956,223 | 5/1976 | Chiang et al. | 260/33.6 AQ |
| 4,028,292 | 6/1977 | Korpman | 260/27 R |
| 4,060,503 | 11/1977 | Feeney et al. | 260/5 |
| 4,080,348 | 3/1978 | Korpman | 260/27 BB |
| 4,096,203 | 6/1978 | St. Clair | 260/876 B |
| 4,097,434 | 6/1978 | Coker, Jr. | 260/23.3 |
| 4,136,071 | 1/1979 | Korpman | 260/27 BB |
| 4,163,077 | 7/1979 | Antonsen et al. | 428/355 |
| 4,250,272 | 2/1981 | Ewins, Jr. et al. | 525/89 |
| 4,288,567 | 9/1981 | Feeney et al. | 525/99 |
| 4,411,954 | 10/1983 | Butch, III et al. | 428/343 |
| 4,460,364 | 7/1984 | Chen et al. | 604/387 |
| 4,514,554 | 4/1985 | Hughes et al. | 526/339 |
| 4,540,415 | 9/1985 | Korpman | 604/390 |
| 4,556,464 | 12/1985 | St. Clair | 204/159.15 |
| 4,650,829 | 3/1987 | Bossaert et al. | 525/99 |
| 4,683,268 | 7/1987 | Ahner | 525/237 |
| 4,810,574 | 3/1989 | Ahner | 604/390 |
| 4,813,947 | 3/1989 | Korpman | 604/387 |
| 4,861,635 | 8/1989 | Carpenter et al. | 604/390 |
| 4,917,929 | 4/1990 | Heinecke | 128/155 |

FOREIGN PATENT DOCUMENTS

1193626 6/1970 United Kingdom.
1438776 6/1976 United Kingdom.

Primary Examiner—David J. Isabella
Assistant Examiner—A. Paul Zuttarelli
Attorney, Agent, or Firm—Gary L. Griswold; Roger R. Tamte; William J. Bond

[57] ABSTRACT

A diaper, adhesive fastening tab which exhibits good peel, quick-stick, shear strength and aging when used with a diaper outer film, either with or without a low adhesion backside. The adhesive used with the fastening tab is based on a composition comprising a slightly aromatic containing aliphatic oil, a styrene/isoprene block copolymer and a solid $C_5$ tackifying resin.

22 Claims, 2 Drawing Sheets

ADHESIVE FASTENING TAB

BACKGROUND AND FIELD OF THE INVENTION

This Invention relates to an improved pressure sensitive adhesive for use with adhesive diaper closure tapes and the like, and more specifically, to a pressure sensitive adhesive composition which provides improved performance characteristics when used in a diaper closure system.

There are numerous patents and literature documents that are directed to the use of block copolymers in adhesive compositions which traditionally include a block copolymer such as an ABA block copolymer and a tackifying resin. U.S. Pat. No. 3,427,269 (Davis), which describes the use of an elastomeric based adhesive comprising at least 100 parts of an ABA block copolymer a rosin ester (10-50 parts) and a coumarone-indene resin (25-50 parts). However, as development of these elastomer based compositions has progressed it has been found that the adhesive properties of these block copolymer based adhesive compositions are extremely sensitive to the particular block copolymer(s) used, and the proportion and type of modifiers such as solid or liquid tackifiers, aromatic or aliphatic tackifiers, plasticizers, extender oils, curing agents and the like.

U.S. Pat. No. 3,932,328 (Korpman) describes the use of prior art adhesive based on an ABA block copolymer with a solid tackifying resin and an extender oil. He describes this composition as unsatisfactory as a pressure-sensitive adhesive(PSA) and proposes a specific composition comprising a styrene-isoprene-styrene (SIS) copolymer and specific proportion of an aliphatic solid tackifier and a liquid tackifier (at 25° C.). Korpman alleged that his adhesive had "satisfactory" adhesion and quick-stick for most applications. The prior art patent Korpman was referring to was U.S. Pat. No. 3,239,478 (Harlan) who discloses both PSA and non-PSA ABA block copolymer based adhesives Harlan only exemplifies a PSA formed of 100 parts of a SIS block copolymer (48 percent S), 75 parts of a 2% aromatic extender oil and 125 parts of a tackifying resin of glycerol ester of polymerized rosin.

U.S. Pat. No. 3,954,692 (Downey et al) also addressed the problems with ABA based adhesive compositions, particularly hot melt pressure sensitive adhesive compositions, particularly problems with providing adequate adhesion and strength properties. Downey et al. was particularly concerned with providing an adhesive with not only adequate tack but good peel strength and good shear strength Downey et al. proposed an SIS block copolymer admixed with conventional extender oils, which were stated as unsatisfactory by Korpman, using a specific tackifying resin. The resin exemplified comprised a polymerized admixture of piperylene and 2-methyl-2-butene, which is marketed, e.g., as Wingtack TM 95, available from Goodyear Chemical Company.

An alleged improvement, for an adhesive designed to be used with porous substrates (e.g., Kraft paper), on the Downey et al. formulation is proposed by U.S. Pat. No. 4,097,434 (Coker) which describes conventional practice as using extending oils with low aromatic content in formulations in which extending oils are employed. Coker states that these formulations have inadequate holding power to porous substrates and proposes a formulation of an ABA copolymer (only SIS is exemplified) with a tackifying resin (only the Downey et al. Wingtack TM 95 is exemplified) with an extending oil with a high aromatic content (above 55%) and a saturates content of less than 15%. The two oils compared were Shellflex TM 371 (non-invention) and Dutrex TM 739 (invention). The Shellflex TM 371 formulations were presented to show formulations with inadequate adhesion properties.

Another variation is proposed in U.S Pat. No. 4,460,364 (Chen et al.) which describes a composition having certain rheological properties that they propose are indicative of ABA based adhesives with tenacious bonding and clean release, where the B block is a polyolefin (only polyethylene-polybutylene exemplified). The SEBS copolymers exemplified are used with a solid tackifying resin and a plasticizing or extending oil. Chen et al. states that these compositions do not sacrifice clean release for tenacity as is stated is typically done in prior art hot melt PSA adhesives. Chen et al. was primarily concerned with an adhesive which could be used in a sanitary napkin without leaving residue adhesive on the undergarment. This rheological approach is also proposed by U.S. Pat. No. 4,719,261 (Bunnelle et al.) who uses the same rheological properties to define a hot melt PSA that allegedly can also be used as an elastic. The specific compositions claimed comprise specific ABA (i.e., SIS) copolymers (45-75%) with both aromatic (2-9%) and aliphatic (25-50%) solid resins.

U.S. Pat. No. 3,935,338 (Robertson et al.) describes an adhesive composition that allegedly has a low enough viscosity to be applied as a hot melt and will have enhanced PSA properties at elevated temperatures. The formulation exemplified as meeting this requirement is an SIS block copolymer (100 parts) with an elastomer block compatible resin (50-200 parts), a reinforcing resin (25-100 parts) and an extending oil (25-100 parts). The patent also discloses compositions excluding the reinforcing resin as counterexample formulations that have inadequate adhesive properties at elevated temperatures.

Korpman has also proposed modifications to his formulations, and approach; U.S. Pat. No. 4,813,947 (use of a ABA(SIS) and a tackifier which is coupled with a specific hot melt landing area); 4,540,415 (use of a SIS a solid tackifier and a phosphatide) and 4,080,348 and 4,136,071 (addition of an SI block copolymer).

Although there exists extensive art on the use of block copolymers in PSA compositions, due to the uncertainty in results and continuing need, the search continues for adhesive formulations with yet improved mixes of properties such as adhesion characteristics, such as quick-stick, tack, shear strength, peel strength and hold; cohesion properties and the ability to maintain these properties at various temperatures and over time. Particularly, there is the continuing need for the identification of adhesive formulations that have a proper mix of adhesive properties such as would make them particularly suitable for use in diaper closure systems. The engineering of diapers is highly specialized. Adhesive closure systems used in this environment ideally should have a particular set of properties. The adhesive tab of the closure system should be designed to readily and quickly attach to the outer polymer film portion of the diaper, which is typically a polyolefin film (e.g., polyethylene or polypropylene), which often has a coating that reduces adhesion thereto. This desire for an adhesive fastening tab with the ability to quickly yet not overly aggressively stick to a treated or untreated polymer film often conflicts with the need for an adhesive bond that has a shear strength such that it will not shift when under stress, as is generated by the user, sufficient yet not overly aggressive peel force resistance, and the ability to allow the fastening tab to be removed and reapplied to the diaper outer film or shell without destruction thereof, which properties are themselves often conflicting. This is complicated by the fact that use of "LAB"(Low Adhesion Backsize) layers such as urethane coatings, often used on diaper frontal tapes, interfere with a fastening tab's adhesive properties.

As such it is a general object of the invention to solve the problems in the diaper closure art by providing diaper fastening tabs with an adhesive formulation directed to solve these problems.

Another object is to provide a diaper closure system using a hot melt PSA with improved field performance characteristics.

Another object is to provide a diaper closure system adhesive formulation showing superior peel strength, quick-stick and shear strength in a diaper system using untreated polyolefin film substrates where the adhesive fastening tab adheres.

Another object is to provide an adhesive formulation having superior peel strength, tackiness, hold and shear strength when the adhesive fastening tab is used to attach to adhesive reduction treated substrates.

These and other objects will be apparent to those skilled in the art by reading the attached specification and by practice of the invention disclosed therein.

SUMMARY OF THE INVENTION

It has been found that a hot melt pressure sensitive adhesive can be provided which has advantageous adhesion and cohesive properties when used on a fastening tab in a diaper closure system which adhesive composition comprises:

(a) 33 to 50 weight percent of an A-B block copolymer of at least one polystyrene block A and at least one polyisoprene block B, wherein the A blocks comprise from 10% to 30% of the copolymer, (b) a solid essentially aliphatic tackifying resin, (c) a predominantly aliphatic plasticizing oil, preferably having from 5 to 45 percent aromatic content, and (d) a ratio of plasticizing oil to tackifying resin of about at least 0.01 to 0.45, (e) the oil to resin ratio being such as to give a composite midblock glass transition temperature(CMTg) of from about 245 to 261 K at 50 weight percent elastomer and from about 254 to 265 K at 33 weight percent elastomer wherein the composition comprises all formulations within the area defined by these CMTg defined oil to resin ratio points on a cartesian system where the CMTg defined oil to tackifier resin ratios are on the x-axis and the percent elastomer is on the y-axis.

It has further been found that certain specific adhesive formulations, within those defined above, yield superior diaper closure system adhesive properties when used with a LAB treated film as the adhesive fastening tab landing area and others yield better adhesive fastening tabs for use in attaching to a non-LAB treated landing area.

Figure 1:
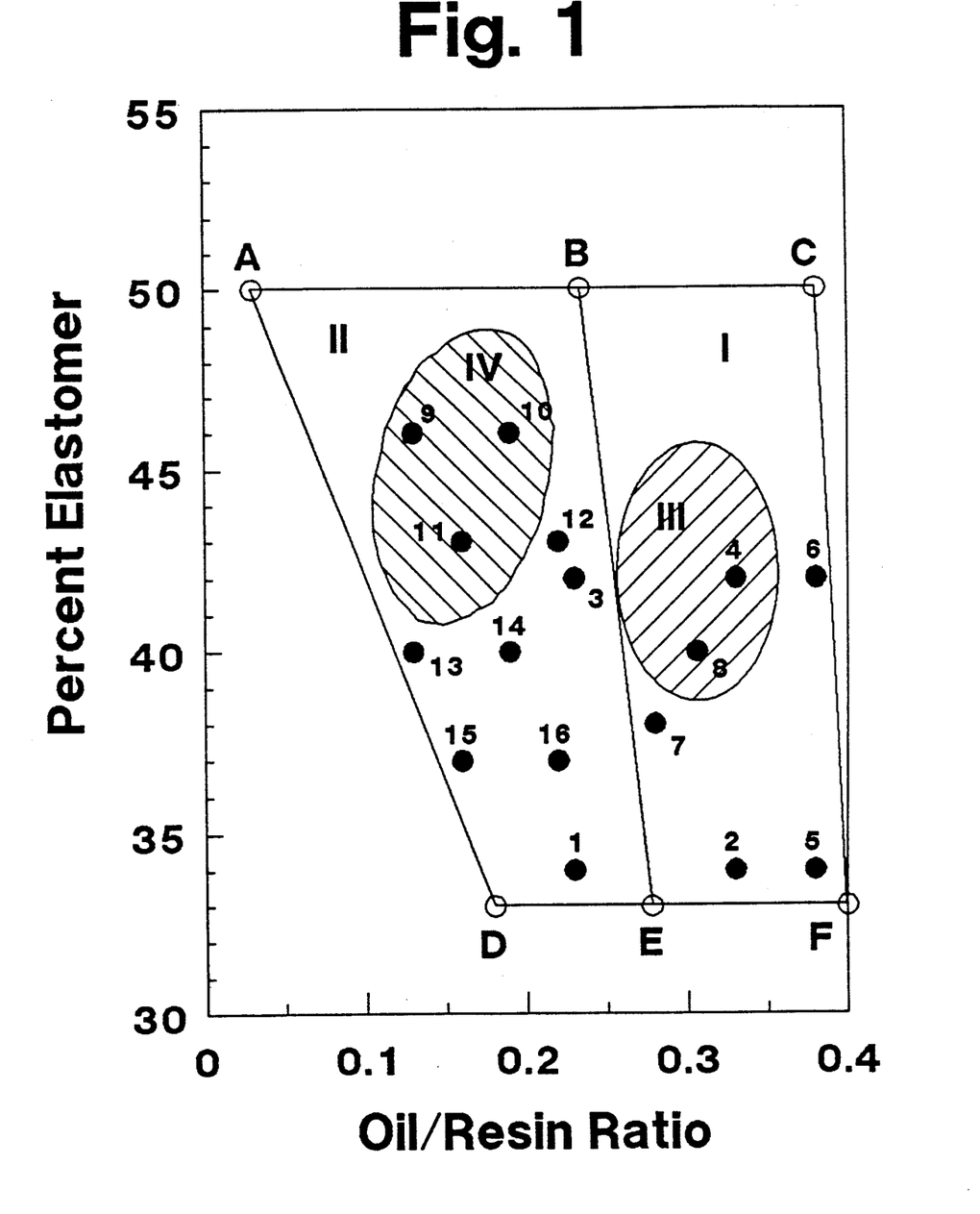
FIG. 1 is a diagram of an area of preferred adhesive compositions.
Figure 2:
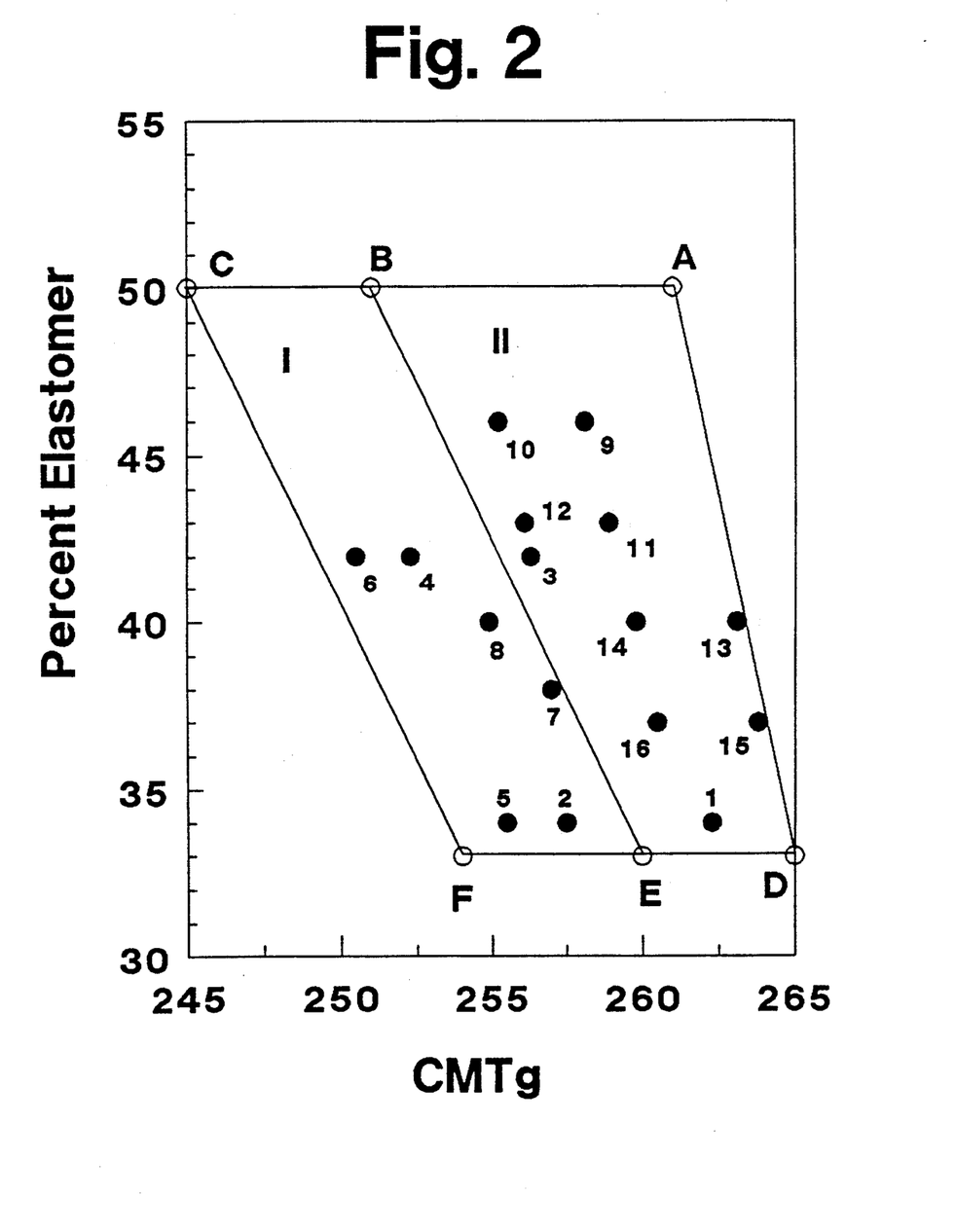
FIG. 2 is a diagram of an area of preferred adhesive compositions based on CMTg.

The x axis in FIG. 1 represents the ratio of Shellflex TM 371 to Wingtack TM Plus and the y axis is the percent elastomer Kraton TM 1111. Points A, B and C are at 50% elastomer with oil/resin ratios of 0.01, 0.23 and 0.38 with composition CTMg values of 261, 251 and 245 Kelvin, respectively. Points D, E and F are at 33% elastomer with oil/resin ratios of 0.19, 0.28 and 0.40 with composition CTMg values of 265, 260 and 254, respectively. Numerals 1-16 correspond to the compositions of Examples 1-16 discussed below. FIG. 2 is a diagram corresponding to FIG. 1 with CMTg on the x axis.

DETAILED DESCRIPTION OF THE PREFERRED EMBODIMENTS

The diaper closure system of the invention can be used with any conventional diaper which uses an adhesive fastening tab to effect closure of the diaper or incontinence device, by attachment to a LAB or non-LAB treated polyolefin or like film. The film can either be the diaper outer shell or a reinforcing film, typically attached to an outer shell. Many diapers are provided with a reinforced area where the tape adheres to the diaper. These reinforcing areas are generally formed of a relatively stiff polymer film, such as a polypropylene film, which is generally attached directly to an outer shell film. These reinforcing films are often provided with what is termed a Low Adhesion Backsize (LAB) by chemical or like treatment. A typical treatment is a urethane coating. These LAB films complicate adhesive diaper closure systems making the selection of the appropriate adhesive to use on the fastening tab exceedingly difficult.

It is believed that the performance of a diaper tape closure adhesive system is related to four different properties of the adhesives of the closure system, the quick-stick adhesion as defined herein, the shear resistance, the peel strenth and the adhesive aging characteristics of the fastening tab. It is important to maintain the proper balance of each of these properties in order to ensure the optimum functionality of the fastening tab in the particular closure system. The preferred ranges for each property will primarily depend on whether the film to which the fastening tab adheres incorporates a low adhesion backsize(LAB) or not. For closure systems where this film incorporates a low adhesion backsize(LAB) such as the urethane type, a high quick-stick to polyethylene is desirable as this will contribute to rapid bond formation of the adhesive fastening tab to the diaper film during application. Rapid bond formation is important, particularly with infant diapers, where rapid closure is desired. Quick-stick values to polyethylene of greater than about 600 grams per inch are preferred in these LAB film systems. With lower quick-stick the tape does not attach to the LAB surface with as much aggressiveness as consumers would prefer. Peel force is also important as too low of a force will run the risk of unfastening while too high of a force makes the fastening tab difficult to remove and can tear the diaper film, particularly thin polyethylene back sheets as are used on many diapers. For LAB films a 135 degree peel force between the fastening tab and diaper film of greater than about 250 grams per inch is preferred, with 350 grams being more preferred. Peel values less than these preferred values may still be functional yet are less desirable as a commercial product.

The lower the peel value the less commercial is the product. The peel is also preferably smooth, as opposed to shocky, at 12 inches per minute. The shear force resistance for a commercial product is preferably at least 300 minutes with a 1 kilogram weight. Shear resistances of less than 300 down to about 100 are still nominally functional yet are not commercially desirable. Shear values much greater than 500 contribute little added functional or commercial benefit to a diaper fastening tab. Adhesives in the lower range of composite midblock glass transition temperatures (CMTg) of the preferred adhesive space, as shown in FIG. 1, are best suited for use in fastening tapes for closure systems employing a frontal tape incorporating an LAB. The preferred cartesian space for these LAB films is that bounded at 33% elastomer by oil/resin ratios that yield CMTg values of 254 to 260 Kelvin and at 50% elastomer, 245 to 251 Kelvin. In FIGS. 1 and 2 this is area I. Most preferred is the area III in FIG. 1 which includes compositions exhibiting the most of the above four properties in the preferred ranges. Preferred area III would also be present in other FIG. 2 for oil/solid $C_5$ resin/SIS elastomer systems within the adhesive compositions for the invention fastening tabs.

The situation is somewhat different for closure systems that incorporate a diaper film, to which the adhesive fastening tab adheres, that does not have an LAB. The LAB allows for convenient manufacturing of a film into a self-wound roll of PSA tape without the use of a liner. The LAB however, does make it more difficult for the fastening tab to adhere to the diaper film, generally a frontal tape. With no LAB present, it is relatively easy for the fastening tab to adhere to the film. In this case, it is more important to have a bond between the fastening tab and the film that is not excessively high, otherwise the end user will perceive the bond level as being too high and the tab as to difficult to remove. There is also the risk of tearing the diaper films. Consequently the 180 degree peel force of adhesion to the film is preferably less than 700–750 grams per inch. Peel force values in excess of 700–750 are still nominally functional however the more the force is above 700–750 the less commercially desirable is a fastening tab in a diaper closure system. This preferred level of peel adhesion minimizes the tendency for the fastening tab to tear conventional polyethylene back sheets of the diaper when, and if, they contact the fastening tab and provides a fastening tab that can be removed by a commercially acceptable level of peel force. The quick-stick to polyethylene of the fastening tab for this type of closure system is less important than for LAB film systems, however higher quick-stick values are preferred. The shear preference is similar to that for a LAB system and shocky peel is likewise not desired. In FIGS. 1 and 2 area II is that preferred for non-LABed film systems, which is defined by oil/resin ratios that yield CMTg values of from about 260 to 265 Kelvin at 33% elastomer and from about 251 to 261 Kelvin at 50% elastomer. Most preferred is area IV in FIG. 1, which includes compositions with the most of the four properties discussed above in their preferred ranges. Again this most preferred region would also be found in FIG. 2 for other oil/solid $C_5$ resin/SIS elastomer systems within the invention.

For closure systems where no frontal tape is present, such as the refastenable closure systems that were prevalent in the disposable diaper market before the advent of frontal tapes, compositions within the middle range of CMTg values illustrated in FIG. 1 also work quite well. The CMTg range at 33% elastomer content should range from 256 to 262 Kelvin, while at 50% elastomer the CMTg should range from 254 to 260 Kelvin. Fastening tabs constructed using adhesives in this range exhibit the balance of properties necessary for a refastenable closure system. The peel adhesion and quick-stick are sufficiently high to form a secure bond, but not so high as to cause the relatively thicker outer polyethylene cover sheets of these diapers to tear upon opening of the closure. Also, the shear resistance of tapes made using this range of adhesive compositions is generally high enough to provide a secure closure throughout the wearing of the diaper.

The preferred adhesive coating thicknesses on the tabs range from 20 to 75 microns, preferably from 25 to 50 microns. With too thin of an adhesive layer thickness, the adhesion properties will be adversely affected, whereas excess coating thicknesses can be wasteful.

Around the preferred minimum shear value the quick-stick of at least 600 grams per inch is also preferred. However, a lower quick-stick is partially offset by a higher shear value, which together gives the user an overall impression as to the aggressiveness and integrity of the adhesive tab when used in a diaper closure system. As such, slightly lower quick-stick values(e.g.,-down to 500) are acceptable with higher shear values.

The block copolymers employed in adhesive compositions for the invention fastening tabs are thermoplastic block copolymers having a linear, graft or radial configuration and having the A blocks and B blocks formed predominantly in what is termed an ABA block copolymer. The A block being a monoalkenyl arene, mainly polystyrene, having a molecular weight between 2,000 and 125,000, preferably between 7,000 and 30,000. The A block content being from about 10 to 50 percent, more preferably between 10 and 30 percent. Other suitable A blocks may be formed from alphamethyl styrene, t-butyl styrene and other ring alkylated styrenes as well as mixtures thereof. B is an elastomeric conjugated diene, namely isoprene, having an average molecular weight of from about 5,000 to about 1,000,000, preferably between about 15,000 to about 300,000 and most preferably from 50,000 to 180,000. Although preferably ABA and AB block copolymers will comprise the majority of the elastomer of the adhesive other conventional diene elastomers may be used to a minor extent, i.e., up to 25 percent of the elastomer, such as natural rubber; butadiene, isoprene or butadiene-styrene rubber; butadiene-acrylonitrile; butyl rubber or block copolymers of these diene elastomers. The block copolymer is used in an amount ranging from 33 to 50 weight percent, preferably at least 38 weight percent of the adhesive composition.

The tackifying resin used is one that is compatible with the elastomeric conjugated diene block and is preferably a tackifying resin having a softening point between 80 and 115° C., such as is produced from polymerization of a stream of aliphatic petroleum derivatives of dienes and monoolefins having 5 carbon atoms as is disclosed in U.S. Pat. Nos. 3,939,328 and 3,954,692, the substance of which are incorporated herein by reference. Preferred are tackifying resins resulting from the copolymerization of a feed comprised predominately of piperylene and 2-methyl-2-butene or isoprene, commercially available as Wingtack TM 95 and Wingtack TM-Plus, respectively, from Goodyear Chemical Co. These resins generally have a minimal amount of aromatic hydrocarbons if any and preferably not more than about 7 percent by weight of aromatic hydrocarbons.

The plasticizing oil is an essentially aliphatic extending oil, preferably containing more than 5 and less than 45% aromatic hydrocarbons and contributes to the performance of the invention diaper closure system adhesive composition. The plasticizing oil can be aliphatic oils such as paraffinic or naphthenic oils.

Generally the oil is used in combination with the solid $C_5$ tackifying resin to provide an oil/resin ratio of from about 0.01 to about 0.45 depending on the oil, tackifier or elastomer used. Of more importance is that the oil to tackifier ratio gives a composition having a composite midblock glass transition temperature (CMTg) of from about 254 to 265 Kelvin at 33 percent elastomer and from about 245 to 261 Kelvin at 50 percent elastomer. These CMTg values define the appropriate oil to tackifier ratios for any particular combination thereof. FIG. 1 demonstrates compositions for use in the invention fastening tab for the combination of a Wingtack TM Plus tackifier resin (a tackifier formed predominately of isoprene and piperylene), Shellflex TM 371 (a naphthenic oil) and Kraton TM 1111 (a styrene-isoprene-styrene copolymer). The invention fastening tab compositions fall into the enclosed space. The minimum and maximum oil/tackifier ratios at 33 and 50 percent elastomer correspond to the above identified maximum and minimum CMTg's where the lower CMTg ratios correspond to the higher oil/tackifier ratios.

The CMTg can be calculated using the Fox Equation from measuring the Tg of the midblock of the elastomeric block copolymer and the measured Tg of each tackifying resin and liquid plasticizer oil. The Tg for each component is measured using a differential scanning calorimeter such as a DSC-7, manufactured by Perkin-Elmer. The Tg is measured on the second heating run using a scan rate of 20 degrees Centigrade per minute. The first heating run is made up to well above the softening point of the test material. The sample is subsequently quenched to well below the Tg of the material. Antioxidants added to the adhesive are not figured into the calculation of the CMTg. The Fox Equation is:

$$\frac{\Sigma_i W_i}{CMTg} = \Sigma_i \frac{W_i}{Tg_i}$$

where $W_i$ is the weight fraction of component i and $Tg_i$ is the glass transition temperature of component i. Only the midblock portion of the block copolymer is included in the calculation of the CMTg. For a styrene/isoprene block copolymer, the midblock portion is the polyisoprene portion of the molecule.

The invention adhesive tabs are particularly advantageous in terms of their ability to retain their adhesion properties over time. Specifically, quick-stick, which is related to the ability of the adhesive to rapidly wet the substrate to which it will attach, tends to decrease only to a relatively minor degree over time. Degradation of quick-stick also reflects the overall adhesion property stability of the adhesive composition. Preferably the adhesives used will exhibit a degradation of quick-stick of less than about 25 percent, and more preferably less than 20 percent, when aged in roll form for 15 days at 50° C. The adhesive compositions used in the invention thus exhibit not only the ability to obtain the often conflicting goals of good initial tack, or quick-stick, good peel resistance, and good shear strength, but also stability of these properties.

The adhesive compositions can also be modified with well known additives such as pigments, fillers, stabilizers and antioxidants for their conventional purposes.

The fastening tab is formed by placing the adhesive described above on a conventional substrate. The fastening tab substrate can suitably be formed of a synthetic polymer such as polyolefins (e.g., polypropylene), polyesters, polyamides or the like. Natural backings such as Kraft paper backings may also be used. The adhesive can be applied by any conventional method including melt coating, gravure, coextrusion, solvent coating and the like.

The following examples are the currently contemplated preferred modes for carrying out the invention and should not be considered as limiting thereof unless otherwise indicated.

EXAMPLES 1-13

The samples were prepared by coating the adhesives as listed in Table 1 onto cast polypropylene films, exhibiting a matte finish. For Examples 1-8 and Counterexample 22, the polypropylene film was 125 microns thick and the adhesives were applied from a melt. For Examples 9-19 and Counterexamples 20, 21 and 23-26, the film was 100 microns thick and the adhesives were coated from a 50% solids solution in toluene in a conventional fashion. In all examples and counterexamples, the thickness of the adhesive is around 40 microns. For each adhesive, 1% by weight of Irganox TM 1010, a hindered phenol antioxidant available from Ciba-Geigy, is added.

The resulting hydrocarbon mixture had the following composition:

TABLE I

| EXAMPLE | KRATON TM 1111 | SHELLFLEX TM 371 | WINGTACK TM PLUS | CMTg |
|---|---|---|---|---|
| 1 | 34 | 12.3 | 53.7 | 262.3 |
| 2 | 34 | 16.4 | 49.6 | 257.5 |
| 3 | 42 | 10.9 | 47.1 | 256.3 |
| 4 | 42 | 14.4 | 43.6 | 252.3 |
| 5 | 34 | 18.2 | 47.8 | 255.5 |
| 6 | 42 | 16.0 | 42.0 | 250.5 |
| 7 | 38 | 13.6 | 48.4 | 257.0 |
| 8 | 40 | 13.8 | 46.2 | 254.9 |
| 9 | 46 | 6.2 | 47.8 | 258.1 |
| 10 | 46 | 8.6 | 45.4 | 255.2 |
| 11 | 43 | 7.9 | 49.1 | 258.9 |
| 12 | 43 | 10.3 | 46.7 | 256.1 |
| 13 | 40 | 6.9 | 53.1 | 263.1 |
| 14 | 40 | 9.6 | 50.4 | 259.8 |
| 15 | 37 | 8.7 | 54.3 | 263.8 |

TABLE I-continued

| EXAMPLE | KRATON 1111 | % OIL | OIL TYPE | PERCENT AROMATICS | WINGTACK PLUS |
|---|---|---|---|---|---|
| 16 | 37 | 11.4 | | 51.6 | 260.5 |
| 17 | 40 | 13.8 | SHELLFLEX 132 | 24 | 46.2 |
| 18 | 40 | 13.8 | SHELLFLEX 212 | 29 | 46.2 |
| 19 | 40 | 13.8 | GASCON 58 | 40 | 46.2 |

| CT. EX. | KRATON 1107 | MINERAL OIL | W-10 | A-25 | W-95 | W+ | E-1310 | CMTg |
|---|---|---|---|---|---|---|---|---|
| 20 | 45.5 | 9 | | | 45.5 | | | 255.6 |
| 21 | 30 | | 20.5 | | | 49 | | 264.9 |
| 22 | 33 | | | 19.2 | | | 47.8 | 264.1 |

| CT. EX. | SOLPRENE 1205 | KRATON 1101 | SHELLFLEX 371 | ZONAREZ A-135 |
|---|---|---|---|---|
| 23 | 33.75 | 11.25 | 9.2 | 45.8 |
| 24 | 35.25 | 11.75 | 7.0 | 47.0 |
| 25 | 32.25 | 10.75 | 7.5 | 49.5 |
| 26 | 32.25 | 10.75 | 11.4 | 45.6 |

W-10 is Wingtack 10, W-95 is Wingtack 95, W+ is Wingtack Plus, A-25 is Zonarez A-25 and E-1310 is Escorez 1310LC.

Kraton 1107 is a polystyrene-isoprenepolystyrene linear block copolymer available from Shell Chemical Co. having a styrene/isoprene ratio of 14/86, approximately 20 percent diblock and 80 percent triblock and a midblock Tg of 215 Kelvin.

Kraton 1111 is a polystyrene-isoprenepolystyrene linear block copolymer available from Shell Chemical Co. having a styrene content of 21 percent and a midblock Tg of 215 Kelvin.

Kraton 1101 and Solprene 1205 are styrene/butadiene block copolymers with midblock Tgs of 188 and 196 Kelvin and available from Shell Chemical Co. and Fina Oil and Chemical Co., respectively.

Escorez 1310LC is a solid $C_5$ s tackifying resin available from Exxon Chemical Corp. having a Tg of 313.5 Kelvin.

Wingtack Plus is a solid $C_5$ tackifying resin having a Tg of 315 Kelvin available from Goodyear Chemical Co.

Wingtack 10 is a liquid $C_5$ hydrocarbon resin with a Tg of 245 Kelvin also from Goodyear.

Zonarez A-25 is a liquid alpha pinene tackifying resin with a Tg of 251 Kelvin available from Arizona Chemical Co.

Zonarez A-135 is a solid alpha pinene resin with a Tg of 367 from Arizona.

Shellflex 371, 132 and 212 are naphthenic oils having about 10%, 24% and 29% aromatics, respectively, measured by clay-gel analysis. The 371 has a Tg of 209 Kelvin. All are available from Shell Chemical Co.

Gascon 58 is a naphthenic oil with an aromatic content of 40% from Lyondell Chemical Co.

The mineral oil in Example 20 is Kaydol White Oil with a Tg of 209 Kelvin from Witco Chemical Co.

TABLE II

| EX | HOLDING POWER | 135 DEG. PEEL | SHEAR BOPP | SHEAR PP | QUICK STICK | 180 PEEL | AGED Q.S. % 15HA, | % CHANGE |
|---|---|---|---|---|---|---|---|---|
| 1 | 1000+ | 110* | 1500+ | 320 | 1065 | 1230 | 885 | −17 |
| 2 | 990 | 160* | 600 | 70 | 925 | 1050 | 755 | −18 |
| 3 | 1000+ | 160* | 1500+ | 650 | 875 | 990 | 750 | −14 |
| 4 | 330 | 275 | 810 | 50 | 810 | 860 | 670 | −17 |
| 5 | 20 | 390 | 110 | 20 | 780 | 820 | 710 | −09 |
| 6 | 30 | 400 | 320 | 30 | 690 | 750 | 580 | −16 |
| 7 | 1000+ | 170* | 1500+ | 160 | 1000 | 1110 | 830 | −17 |
| 8 | 1000+ | 280 | 1200 | 90 | 830 | 1000 | 690 | −17 |
| 9 | 40 | 150* | 1500+ | 1500+ | 600 | 660 | 410 | −15 |
| 10 | | | | 340 | 520 | 580 | | |
| 11 | | | | 980 | 690 | 690 | | |
| 12 | | | | 40 | 670 | 660 | | |
| 13 | | | | 1500+ | 750 | 860 | | |
| 14 | | | | 80 | 790 | 860 | | |
| 15 | | | | 540 | 760 | 890 | | |
| 16 | | | | 50 | 800 | 820 | | |
| 17 | | 360 | 850 | | 740 | | | |
| 18 | | 380 | 910 | | 720 | | | |
| 19 | | 290 | 1290 | | 750 | | | |
| Counterexamples | | | | | | | | |
| 20 | 70 | 330 | 1500+ | 900 | 480 | 790 | | |
| 21 | 270 | 180* | | 60 | 640 | 790 | | |
| 22 | 1000+ | 110* | 1000 | | 1140 | 1580 | 915 | −42 |
| 23 | | <100* | 1500+ | 1500+ | 1020 | 1040 | 700 | −31 |
| 24 | | <100* | 1500+ | 1500+ | 1525 | 1050 | 950 | −38 |
| 25 | | <100* | 1500+ | 1500+ | 450 | 990 | 260 | −42 |

TABLE II-continued

| EX | HOLDING POWER | 135 DEG. PEEL | SHEAR BOPP | SHEAR PP | QUICK STICK | 180 PEEL | AGED Q.S. % 15HA, | % CHANGE |
|---|---|---|---|---|---|---|---|---|
| 26 | | <100* | 1500+ | 1500+ | 1030 | 1020 | 710 | −31 |

*designates shocky peel

TEST METHODS

135 Degree Peel from Frontal Tape

The peel adhesion test is a 135 degree peel from a smooth frontal tape surface of biaxially oriented polypropylene(BOPP), having a LAB on it. This LAB is a copolymer of vinyl acetate and vinyl alcohol where some of the alcohol groups in the polymer backbone have been reacted with octadecyl isocyanate. The peel rate is 12 inches per minute. The tape samples are rolled down onto the frontal tape substrate using two passes of a 4.5 pound roller. This test is a variation on PSTC-5. The data is reported in grams per inch.

Shear from Frontal Tape Substrate

The shear adhesion is measured by determining the length of time it takes for a 1 inch by 1 inch sample to shear off a frontal tape substrate under a 1 kilogram load. The frontal tape is either a smooth frontal tape(BOPP) with a LAB as described above or a matte polypropylene(PP) without an LAB. The frontal tape is laminated to a pressure sensitive tape in order to enhance the stiffness of the substrate. The tape used for reinforcement for these experiments was Release Tape Y-9378, manufactured by 3M Co. On the side opposite the reinforcing tape, a one square inch area of the test tape is rolled down onto the frontal tape using 2 passes of a 4.5 pound roller. The laminated substrate and the test tape are hung vertically in a 40° C. oven and a 1 kilogram weight is hung from the test tape. The time in minutes for the weight to drop is used as the measure of the shear adhesion.

180 Degree Peel

The 180 degree peel adhesion test is run using a matte finish frontal tape where the frontal tape is constructed from polypropylene and has no LAB. The peel rate is 12 inches per minute. The tape samples are rolled down onto the frontal rape substrate using two passes of a 4.5 pound roller. The 180 degree peel adhesion is reported in grams per inch.

Quick-Stick Test

The quick-stick of the examples was measured using the following test. The tape samples were rolled down onto a smooth polyethylene substrate using a 100 gram roller. The light roll down force allows for measuring quick-stick, whereas a heavy roll down is more indicative of peel adhesion. The polyethylene substrate is then peeled away from the tape sample, eliminating tape backing effects. The quick-stick value is reported in grams per inch. Some of the samples were also tested for quick-stick after aging in roll form for 15 days at 50 Centigrade.

Holding Power Test

The holding power test is a measure of how well a diaper closure system will perform when subject to peel type forces when applied with only a light application pressure. In this test a 1 "×1" tape sample is rolled down onto an embossed polyethylene sheet similar to that used for disposable diaper backsheets with a rolldown force of 250 grams. The polyethylene sheet measures 2 "×4" and is supported only along the minor axis at either end of the sheet. The tape sample is rolled down in the middle of this polyethylene sheet. The tape sample and the polyethylene substrate are suspended with the tape on the under side of the sheer. A 200 gram weight is hung from the tape sample, yielding an effective peel angle of 90 degrees. The Holding Power value is the time in minutes for the tape sample to peel off of the polyethylene sheet. Six replicates were run for each example and the time values in minutes averaged to give the value reported.

Counterexample 20 corresponds to preferred Example 10 and shows the effect of using a non-aromatic oil on diaper fastening tape performance. Example 10 is a composition that with an oil having an aromatic content gave results within the preferred range of the four properties discussed above for a non-LAB film. However the Example 10 composition in Counterexample 20 using a non-aromatic oil gave less than preferred quick-stick and 180 degree peel. This example corresponds to sample 10 of Example 3 of the above discussed Downey patent which is his only proposed PSA for general application, and his only example containing oil. Although this composition could be used in the invention diaper fastening tab it is less desirable than those based on the preferred composition using a slightly aromatic oil.

Counterexamples 21-22 represent optimized commercial compositions for diaper fastening tabs based on different composition chemistries. As can be seen the invention fastening tabs performed on a par with if not superior to these prior tabs.

Counterexamples 23-26 show the performance characteristics of diaper fastening tabs made with adhesives based on extender oil containing compositions other than those of the invention diaper fastening tabs. Namely the elastomer component has been substituted with a common block elastomer used in PSA adhesive compositions, SBS, while still using composition ratios within the invention preferred range, at least for Examples 23-25, shown as area IV in FIG. 1. These Examples showed excessive 180 degree peel and poor 135 degree peel with bad aging performance.

Other embodiments of the invention will be apparent to those skilled in the art from the consideration of the specification of or practice of the invention disclosed herein. It is intended that the specifications and examples can be considered as exemplary, with the true scope and spirit of the invention being indicated by the following claims.

What is claimed is:

1. A diaper fastening tab comprising a substrate and an adhesive layer, the adhesive composition of said adhesive layer comprising;
   (a) 33 to 50 weight percent of an elastomer component comprised of a block copolymer of A blocks derived from styrene and B blocks derived from isoprene,
   (b) a solid tackifying resin comprised predominantly of $C_5$ hydrocarbons, and
   (c) an aliphatic oil having from about 5 to 45 percent aromatic hydrocarbon content, wherein the ratio of aliphatic oil to solid tackifying resin is from about 0.01 to 0.45 and wherein said block copolymer, tackifying resin and aliphatic oil composition ratios are defined by the cartesian space enclosed by those compositions having CMTg values of 254 to 265 Kelvin at 33 percent by weight elastomer content and CMTg values of 245 to 261 Kelvin at 50 weight percent elastomer, defined by points A-F in FIG. 2.

2. The diaper fastening tab of claim 1 wherein said A blocks comprise 10 to 30 weight percent of said copolymer.

3. The diaper fastening tab of claim 1 wherein said tackifying resin is a polymerized structure derived predominantly from piperylene and either 2-methyl-2-butene or isoprene.

4. The diaper fastening tab of claim 1 wherein said solid $C_5$ resin has a softening point of from 80 to 115 degrees Centigrade.

5. The diaper fastening tab of claim 1 comprising at least 38 percent of said elastomer.

6. The diaper fastening tab of claim 1 wherein said CMTg values range from about 254 to 260 Kelvin at 33% elastomer and from about 245 to 251 Kelvin at 50% elastomer for adhering said tab to a diaper film with a LAB defined by points B, C, E and F in FIG. 2.

7. The diaper fastening tab of claim 1 wherein said CMTg values range from about 260 to 265 Kelvin at 33% elastomer and from about 251 to 261 Kelvin at 50% elastomer for adhering said tab to a diaper film without a LAB defined by points A, B, D and E in FIG. 2.

8. The diaper fastening tab of claim 6 wherein said CMTg values and said percent elastomer of said adhesive composition correspond to those defined by area III in FIG. 1.

9. The diaper fastening tab of claim 7 wherein said CMTg values and said percent elastomer of said adhesive composition correspond to those defined by area IV in FIG. 1.

10. A diaper comprising the diaper fastening tab of claim 1 further comprising a diaper with an outer film to which the fastening tab attaches.

11. The diaper of claim 10 wherein the outer film is an outer sheet.

12. The diaper of claim 11 wherein the outer sheet is polyethylene

13. The diaper of claim 10 wherein the outer film is a reinforcing film attached to an outer sheet.

14. A diaper comprising the diaper fastening tab of claim 8 further comprising a diaper with an outer LAB film to which the fastening tab attaches.

15. The diaper of claim 14 wherein the outer film is a reinforcing film attached to an outer sheet.

16. A diaper comprising the diaper fastening tab of claim 9 further comprising a diaper with an outer non-LAB film to which the fastening tab attaches.

17. The diaper of claim 16 wherein the outer film is an outer polyethylene sheet.

18. An adhesive composition comprising;
 (a) 33 to 50 weight percent of an elastomer component comprised of a block copolymer of A blocks derived from styrene and B blocks derived from isoprene,
 (b) a solid tackifying resin comprised predominantly of $C_5$ hydrocarbons, and
 (c) an aliphatic oil having from about 5 to 45 percent aromatic hydrocarbon content, wherein the ratio of aliphatic oil to solid tackifying resin is from about 0.01 to 0.45 and wherein said block copolymer, tackifying resin and aliphatic oil composition ratios are defined by the cartesian space enclosed by those compositions having CMTg values of 254 to 260 Kelvin at 33 percent by weight elastomer content and CMTg values of 245 to 251 Kelvin at 50 weight percent elastomer, defined by points B, C, E and F in FIG. 2.

19. The adhesive composition of claim 18 wherein said block copolymer A blocks comprise 10 to 30 weight percent of said copolymer.

20. The adhesive composition of claim 18 wherein said tackifying resin is a polymerized structure derived predominantly from piperylene and either 2-methyl-2-butene or isoprene.

21. The adhesive composition of claim 18 wherein said solid $C_5$ resin has a softening point of from 80 to 115 degrees Centigrade.

22. The adhesive composition of claim 18 wherein said CMTg values and said percent elastomer of said adhesive composition correspond to those defined by area III in FIG. 1.

* * * * *

UNITED STATES PATENT AND TRADEMARK OFFICE
CERTIFICATE OF CORRECTION

PATENT NO. : 5,019,071

DATED : May 28, 1991

INVENTOR(S) : Bany et al.

It is certified that error appears in the above-identified patent and that said Letters Patent is hereby corrected as shown below:

On the cover page, add "Allen L. Noreen, Lake Elmo, Minnesota" as an additional inventor.

Column 1, line 40, delete "adhesives Harlan" and insert therefor --adhesives. Harlan--.

Column 9, line 26, delete "polystyrene-isoprenepolystyrene" and insert therefor --polystyrene-isoprene-polystyrene--.

Column 9, line 31, delete "polystyrene-isoprenepolystyrene" and insert therefor --polystyrene-isoprene-polystyrene--.

UNITED STATES PATENT AND TRADEMARK OFFICE
CERTIFICATE OF CORRECTION

PATENT NO. : 5,019,071

DATED : May 28, 1991

INVENTOR(S) : Bany et al.

It is certified that error appears in the above-identified patent and that said Letters Patent is hereby corrected as shown below:

Column 11, line 43, delete "rape" and insert therefor --tape--.

Column 12, line 10, delete "sheer" and insert therefor --sheet--.

Signed and Sealed this

Third Day of November, 1992

Attest:

DOUGLAS B. COMER

*Attesting Officer*     Acting Commissioner of Patents and Trademarks